US00PP17948P2

(12) United States Plant Patent

White et al.

(10) Patent No.: US PP17,948 P2
(45) Date of Patent: Aug. 28, 2007

(54) *PHYGELIUS* PLANT NAMED 'BLACHER'

(50) Latin Name: *Phygelius hybrida*
Varietal Denomination: Blacher

(75) Inventors: Anthony Robin White, Alresford (GB); Susan White, Alresford (GB)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/323,166

(22) Filed: Dec. 30, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

GTITM UPOVROM Citation for 'Blacher' as per QZ PBR 20040760; Jun. 15, 2004.*

* cited by examiner

*Primary Examiner*—Kent Bell
(74) *Attorney, Agent, or Firm*—C. A. Whealy

(57) ABSTRACT

A new and distinct cultivar of *Phygelius* plant named 'Blacher', characterized by its upright plant habit; freely flowering habit; and large red-colored flowers.

2 Drawing Sheets

Botanical designation: *Phygelius hybrida.*
Cultivar denomination: 'Blacher'.

BACKGROUND OF THE INVENTION

The present Invention relates to a new and distinct cultivar of *Phygelius* plant, botanically known as *Phygelius hybrida,* and hereinafter referred to by the cultivar name Blacher.

The new *Phygelius* is a product of a planned breeding program conducted by the Inventors in Kilmeston, Alresford, United Kingdom. The objective of the breeding program is to create new freely flowering *Phygelius* with attractive flower coloration.

The new *Phygelius* originated from a cross-pollination made by the Inventors in Kilmeston, Alresford, United Kingdom in 1998, of an unnamed selection of *Phygelius rectus,* not patented, as the female, or seed parent, with the *Phygelius aequalis* cultivar Sensation, not patented, as the male, or pollen parent. The new *Phygelius* was discovered and selected as a single plant from the resulting progeny of the cross-pollination in a controlled environment in Kilmeston, Alresford, United Kingdom in 2000.

Asexual reproduction of the new cultivar by softwood cuttings since 2000, in Kilmeston, Alresford, United Kingdom has shown that the unique features of this new *Phygelius* are stable and reproduced true to type in successive generations.

SUMMARY OF THE INVENTION

Plants for the cultivar Blacher have not been observed under all possible environmental conditions. The phenotype may vary somewhat with variations in environment such as temperature and light intensity without, however, any variance in genotype.

The following traits have been repeatedly observed and are determined to be the unique characteristics of 'Blacher'.

These characteristics in combination distinguish 'Blacher' as a new and distinct cultivar:

1. Upright plant habit.
2. Freely flowering habit.
3. Large red-colored flowers.

Plants of the new *Phygelius* differ primarily from plants of the parents in flower color as plants of the female parent selection have orange red-colored flowers and plants of the male parent, the cultivar Sensation, have red purple-colored flowers.

Plants of the new *Phygelius* can be compared to plants of the cultivar Devils Tears, not patented. In side-by-side comparisons conducted in Kilmeston, Alresford, United Kingdom, plants of the new *Phygelius* differed from plants of the cultivar Devils Tears in the following characteristics:

1. Plants of the new *Phygelius* and the cultivar Devils Tears differed in flower color as plants of the cultivar Devils Tears had orange red-colored flowers.
2. Flower throats of plants of the new *Phygelius* were yellow-green in color whereas flower throats of plants of the cultivar Devils Tears were yellow in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Phygelius.*

The photograph on the first sheet comprises a side perspective view of a typical plant of 'Blacher' grown in a container.

The photograph at the top of the second sheet is a close-up view of a typical flowering stem of 'Blacher'.

The photograph at the bottom of the second sheet is a close-up view of a typical leaf of 'Blacher'.

DETAILED BOTANICAL DESCRIPTION

Plants of the cultivar Blacher have not been observed under all possible environmental conditions. The phenotype may vary somewhat with variations in environment such as temperature and light intensity, without, however, any variance in genotype. The aforementioned photographs and following observations and measurements describe plants grown during the summer in Rijpwetering, The Netherlands, under commercial practice in an outdoor nursery with day temperatures ranging from 18° C. to 32° C. and night temperatures ranging from 10° C. to 18° C. Plants used for the photographs and description were about one year old. In the following description, color references are made to The Royal Horticultural Society Colour Chart, 2001 Edition, except where general terms of ordinary dictionary significance are used.

Botanical classification: *Phygelius hybrida* cultivar Blacher.

Parentage:

*Female parent.*—Unnamed selection of *Phygelius rectus,* not patented.

*Male parent.*—*Phygelius aequalis* cultivar Sensation, not patented.

Propagation:

*Type cutting.*—Softwood cuttings.

*Time to initiate roots.*—About four to five weeks at 15° C.

*Root description.*—Fine, fibrous; gray white in color.

*Rooting habit.*—Freely branching; dense.

Plant description:

*Form.*—Perennial flowering plant; upright plant habit. Freely basal branching habit; about 14 lateral branches per plant.

*Plant height.*—About 53 cm.

*Plant diameter.*—About 35.5 cm.

*Vigor.*—Moderately vigorous.

*Lateral branches.*—Length: About 14 cm. Diameter: About 2.5 mm. Internode length: About 4.4 cm. Texture: Smooth, glabrous. Color: 177D overlain with 144C to 144D to 177A to 177B.

*Foliage description.*—Arrangement: Opposite, simple. Length: About 5.9 cm. Width: About 3.1 cm. Shape: Ovate. Apex: Acute. Base: Attenuate. Margin: Serrate. Texture, upper and lower surfaces: Smooth, glabrous. Venation pattern: Pinnate. Color: Developing leaves, upper surface: 137A. Developing leaves, lower surface: 137C. Fully expanded leaves, upper surface: 137A to 137B. Fully expanded leaves, lower surface: 138B. Venation, upper surface: 143A. Venation, lower surface: 145A to 145B. Petiole length: About 1.7 cm. Petiole diameter: About 1.5 mm. Petiole texture, upper and lower surfaces: Smooth, glabrous. Petiole color, upper and lower surfaces: 177A.

Flower description:

*Flower type and habit.*—Single salverform flowers arranged in terminal panicles. Freely flowering habit, usually about 67 flowers per panicle. Flowers pendulous. Flowers not persistent. Flowers not fragrant.

*Natural flowering season.*—Flowering continuous from July to early August in The Netherlands. Plants start flowering about nine months after planting.

*Flower longevity.*—Flowers last about one week on the plant.

*Inflorescence length.*—About 31 cm.

*Inflorescence width.*—About 14.5 cm.

*Flower diameter.*—About 1.5 cm.

*Flower depth.*—About 5.4 cm.

*Flower buds.*—Length: About 2.6 cm. Diameter: About 5 mm. Shape: Narrowly oblong to obovate. Color: 53D; towards the apex, 60C.

*Corolla.*—Shape/arrangement: Tubular; five fused petals. Petal apices: Broadly acute. Petal margin: Entire. Petal length: About 4.1 cm. Petal width: About 5 mm. Texture, upper and lower surfaces of petal lobes: Smooth, glabrous. Color: When opening, inner surface: Tube, 38D; base of petal lobe, 4D to 5D; towards the apex, 53A; at the apex, 59A. When opening, outer surface: 53D; towards the base, 53C. Fully opened, inner surface: Tube, 38D; base of petal lobe, 4D to 5D; towards the apex, 59C. Fully opened, outer surface: 53D; towards the base, 53C; color becoming closer to 60A with development.

*Calyx.*—Length: About 8 mm. Diameter: About 9 mm. Shape: Campanulate, five parted. Sepal apex: Acute. Sepal margin: Entire. Sepal texture, upper and lower surfaces: Smooth, glabrous. Color, upper surface: 144B to 144C; apices flushed with 183B. Color, lower surface: 183A to 200B.

*Peduncles.*—Length: About 31 cm. Diameter: About 4 mm. Strength: Strong. Angle: Primary flowering stems, erect; secondary flowering stems, about 60° from the stem. Color: N186C.

*Pedicels.*—Length: About 1.8 cm. Diameter: About 1 mm. Strength: Strong. Angle: About 35° from the stem. Color: N186C.

*Reproductive organs.*—Androecium: Stamen quantity: Four per flower. Filament length: About 1 cm. Anther length: About 4 mm. Anther shape: Oval. Anther color: Between 147A and 201B. Pollen amount: Scarce. Pollen color: Yellow green. Gynoecium: Pistil quantity: One per flower. Pistil length: About 5.4 cm. Style length: About 5.3 cm. Style color: 60B to 187B. Stigma color: 187A. Ovary color: 146B to 146C.

*Seeds/fruits.*—Seed and fruit development has not been observed.

Disease/pest resistance: Plants of the new *Phygelius* have not been observed to be resistant to pathogens and pests common to *Phygelius.*

Temperature tolerance: Plants of the new *Phygelius* have been observed to tolerate temperatures from about 0° C. to 35° C.

It is claimed:

1. A new and distinct cultivar of *Phygelius* plant named 'Blacher', as illustrated and described.

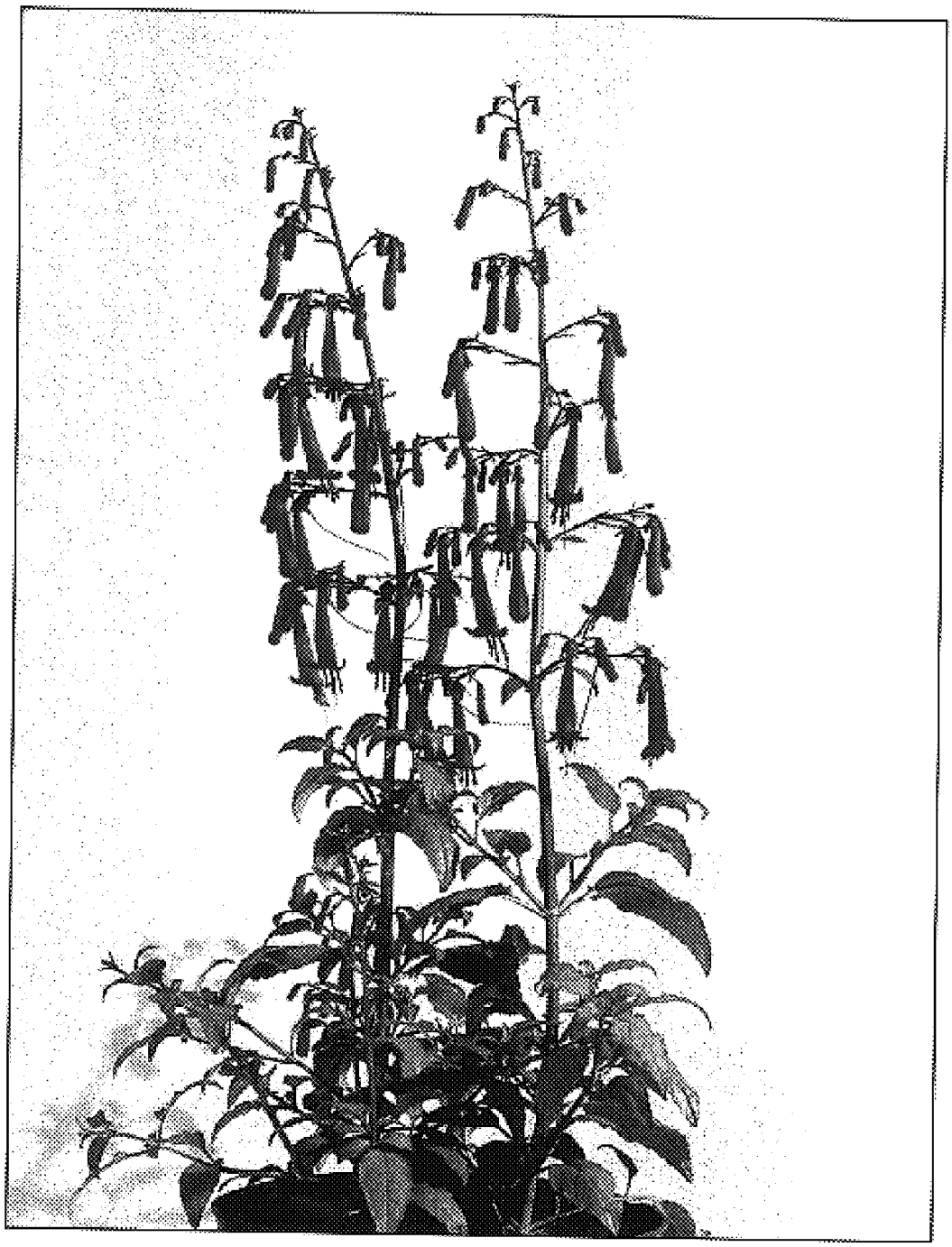

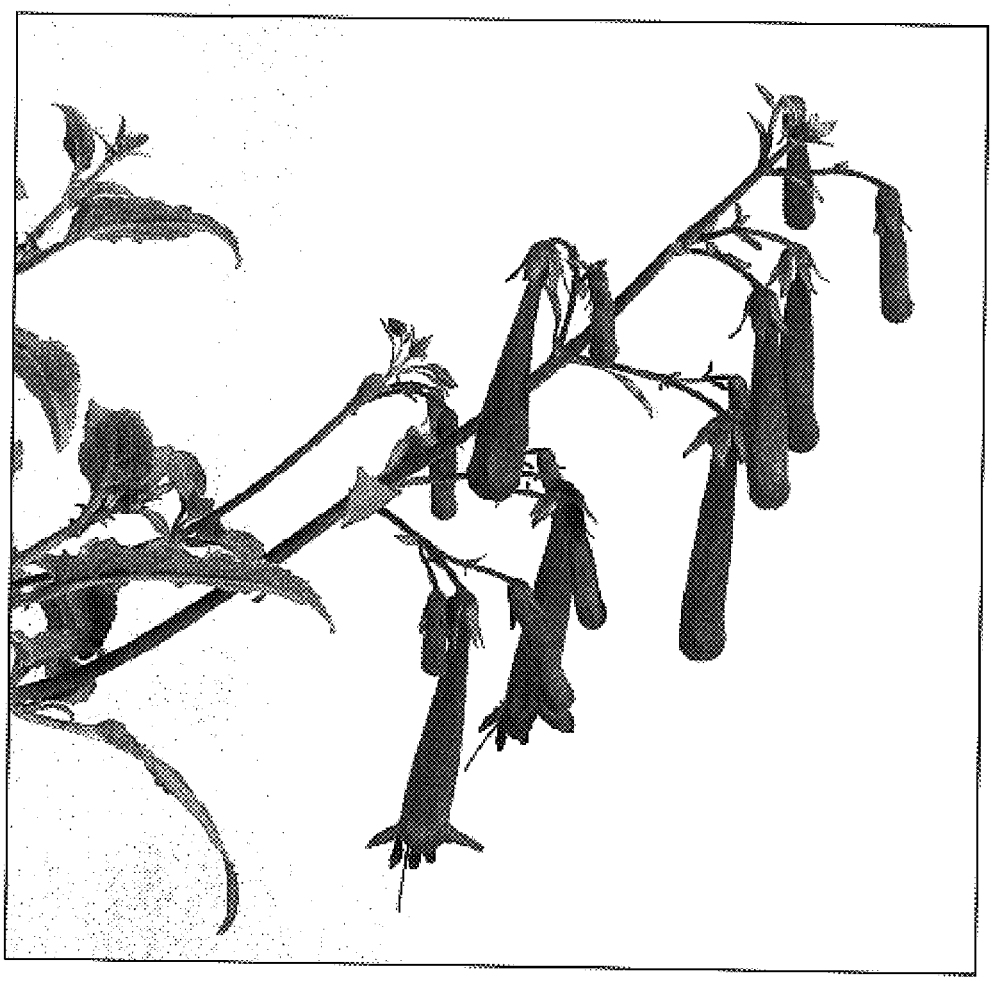
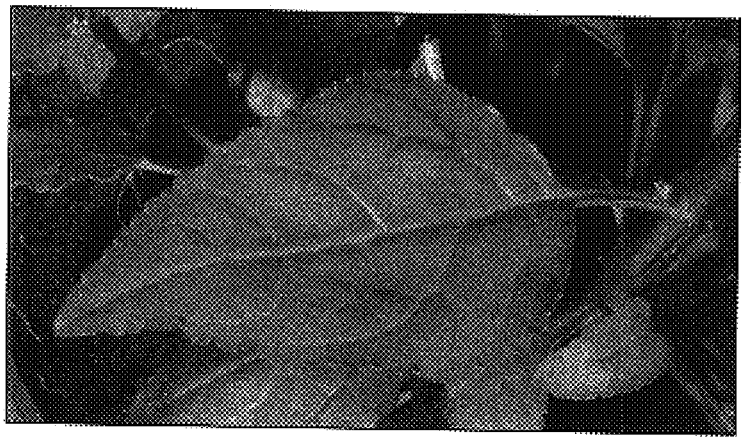

* * * * *